United States Patent
Sianawati

(10) Patent No.: US 8,722,689 B2
(45) Date of Patent: May 13, 2014

(54) SYNERGISTIC COMBINATION OF FLUMETSULAM OR DICLOSULAM WITH DIIODOMETHYL-P-TOLYLSULFONE

(75) Inventor: Emerentiana Sianawati, Vernon Hills, IL (US)

(73) Assignee: Dow Global Technologies LLC, Midland, MI (US)

( * ) Notice: Subject to any disclaimer, the term of this patent is extended or adjusted under 35 U.S.C. 154(b) by 420 days.

(21) Appl. No.: 13/289,289

(22) Filed: Nov. 4, 2011

(65) Prior Publication Data

US 2012/0115888 A1 May 10, 2012

Related U.S. Application Data

(60) Provisional application No. 61/411,523, filed on Nov. 9, 2010.

(51) Int. Cl.
| | |
|---|---|
| *A01N 43/90* | (2006.01) |
| *A01N 41/10* | (2006.01) |
| *A01N 31/08* | (2006.01) |
| *A01N 37/38* | (2006.01) |
| *A01N 25/08* | (2006.01) |
| *A01N 25/04* | (2006.01) |
| *A01N 25/32* | (2006.01) |
| *A01N 59/02* | (2006.01) |
| *A01N 37/10* | (2006.01) |
| *A01N 25/02* | (2006.01) |

(52) U.S. Cl.
CPC ............ *A01N 31/08* (2013.01); *A01N 37/38* (2013.01); *A01N 25/02* (2013.01); *A01N 25/08* (2013.01); *A01N 25/04* (2013.01); *A01N 25/32* (2013.01); *A01N 59/02* (2013.01); *A01N 37/10* (2013.01)
USPC ...................................... 514/259.31; 514/709

(58) Field of Classification Search
USPC ............................................. 514/259.31, 709
See application file for complete search history.

(56) References Cited

U.S. PATENT DOCUMENTS

| | | |
|---|---|---|
| 3,615,745 A | 10/1971 | Crovetti et al. |
| 5,591,760 A | 1/1997 | Hsu |
| 2003/0005508 A1 | 1/2003 | Hourihan et al. |
| 2004/0198713 A1 | 10/2004 | Heer et al. |
| 2004/0204405 A1 | 10/2004 | Bruns et al. |
| 2004/0219128 A1 | 11/2004 | Batdorf |
| 2006/0135472 A1 | 6/2006 | Annis |
| 2009/0042960 A1 | 2/2009 | Bruns et al. |
| 2009/0192219 A1 | 7/2009 | Uhr et al. |
| 2010/0189811 A1 | 7/2010 | Baum et al. |
| 2010/0297204 A1 | 11/2010 | Uhr et al. |
| 2012/0136010 A1 | 5/2012 | Sianawati et al. |

FOREIGN PATENT DOCUMENTS

| | | |
|---|---|---|
| EP | 1468608 | 10/2004 |

OTHER PUBLICATIONS

Netherland, et al. "Potential for Selective Activity of the ALS Inhibitors Penoxsulam, Bispyribac-sodium and Imazamox on algae Responsible for Harmful Blooms", J. Aquat., pp. 147-150 (2008).
"Flumetsulam" The e-Pesticide manual, v. 5.0, (2009).
"Diclosulam" The e-Pesticide manual, v. 5.0, (2009).
"Penoxsulam" The e-Pesticide manual, v. 5.0, (2009).

*Primary Examiner* — San-Ming Hui
(74) *Attorney, Agent, or Firm* — Kenneth Crimaldi

(57) ABSTRACT

A synergistic antimicrobial composition containing flumetsulam or diclosulam; and diiodomethyl-p-tolylsulfone.

5 Claims, No Drawings

SYNERGISTIC COMBINATION OF FLUMETSULAM OR DICLOSULAM WITH DIIODOMETHYL-P-TOLYLSULFONE

This invention relates to combinations of biocides, the combinations having greater activity than would be observed for the individual antimicrobial compounds.

Use of combinations of at least two antimicrobial compounds can broaden potential markets, reduce use concentrations and costs, and reduce waste. In some cases, commercial antimicrobial compounds cannot provide effective control of microorganisms, even at high use concentrations, due to weak activity against certain types of microorganisms, e.g., those resistant to some antimicrobial compounds. Combinations of different antimicrobial compounds are sometimes used to provide overall control of microorganisms in a particular end use environment. For example, U.S. Pat. No. 5,591,760 discloses a combination of 3-iodo-2-propynyl-butylcarbamate (IPBC) and 4,5-dichloro-2-n-octyl-4-isothiazolin-3-one (DCOIT), but this reference does not suggest any of the combinations claimed herein. Moreover, there is a need for additional combinations of antimicrobial compounds having enhanced activity against various strains of microorganisms to provide effective control of the microorganisms, especially in dry film coatings. The problem addressed by this invention is to provide such additional combinations of antimicrobial compounds.

STATEMENT OF THE INVENTION

The present invention is directed to a synergistic antimicrobial composition comprising: (a) flumetsulam or diclosulam; and (b) diiodomethyl-p-tolylsulfone (DIMTS); wherein a weight ratio of flumetsulam to diiodomethyl-p-tolylsulfone is from 8:1 to 1:15 and a weight ratio of diclosulam to diiodomethyl-p-tolylsulfone is from 12:1 to 2:1 or 1:1.5 to 1:15.

DETAILED DESCRIPTION OF THE INVENTION

As used herein, the following terms have the designated definitions, unless the context clearly indicates otherwise. Flumetsulam is N-(2,6-difluorophenyl)-5-methyl[1,2,4]triazolo[1,5-a]pyrimidine-2-sulfonamide. Diclosulam is N-(2,6-dichlorophenyl)-5-ethoxy-7-fluoro[1,2,4]triazolo[1,5-c]pyrimidine-2-sulfonamide. The term "antimicrobial compound" refers to a compound capable of inhibiting the growth of or controlling the growth of microorganisms; antimicrobial compounds include bactericides, bacteristats, fungicides, fungistats, algaecides and algistats, depending on the dose level applied, system conditions and the level of microbial control desired. The term "microorganism" includes, for example, fungi (such as yeast and mold), bacteria and algae. The following abbreviations are used throughout the specification: ppm=parts per million by weight (weight/weight), mL=milliliter, ATCC=American Type Culture Collection, and MIC=minimum inhibitory concentration. Unless otherwise specified, temperatures are in degrees centigrade (° C.), and references to percentages are by weight (wt %). Percentages of antimicrobial compounds in the composition of this invention are based on the total weight of active ingredients in the composition, i.e., the antimicrobial compounds themselves, exclusive of any amounts of solvents, carriers, dispersants, stabilizers or other materials which may be present.

Preferably, when the antimicrobial composition comprises flumetsulam and DIMTS, a weight ratio of flumetsulam to DIMTS is from 7:1 to 1:15, preferably from 8:1 to 1:12; preferably from 7:1 to 1:12, preferably from 6:1 to 1:15; preferably from 6:1 to 1:12; preferably from 7:1 to 1:10; preferably from 6:1 to 1:10.

Preferably, when the antimicrobial composition comprises diclosulam and DIMTS, a weight ratio of diclosulam to DIMTS is from 10:1 to 2:1 or 1:1.5 to 1:15; preferably from 10:1 to 2:1 or 1:2 to 1:15; preferably from 10:1 to 2:1 or 1:2 to 1:12; preferably from 10:1 to 3:1 or 1:2 to 1:12; preferably from 10:1 to 3:1 or 1:2 to 1:10.

Preferably, diclosulam in combination with DIMTS is used to inhibit growth of algae in an aqueous medium. Preferably, the ratio of diclosulam to DIMTS is from 10:1 to 2:1 or 1:1.5 to 1:15; preferably from 10:1 to 2:1 or 1:2 to 1:15; preferably from 10:1 to 2:1 or 1:2 to 1:12; preferably from 10:1 to 3:1 or 1:2 to 1:12; preferably from 10:1 to 3:1 or 1:2 to 1:10.

The antimicrobial compositions described above may contain either or both of flumetsulam and diclosulam and/or other biocides. Typically, the antimicrobial compositions are used to inhibit growth of algae and/or fungi.

Preferably, the antimicrobial combinations of this invention are incorporated into liquid compositions, especially dispersions of polymers in aqueous media. The biocide combinations are particularly useful in preservation of building materials, e.g., adhesives, caulk, joint compound, sealant, wallboard, etc), paints, coatings, polymers, plastics, synthetic and natural rubber, paper products, fiberglass sheets, insulation, exterior insulating finishing systems, roofing and flooring felts, building plasters, wood products and wood-plastic composites. Preferably, the antimicrobial compositions are latex paints or other liquid coating compositions containing the biocide combinations disclosed herein. The biocide combinations are useful for preservation of the dry film coating resulting after application of a paint or other liquid coating composition. Preferably, the antimicrobial composition is an acrylic latex paint comprising one or more of the biocide combinations disclosed herein, or the dry film coating resulting from application of the paint to a surface.

Typically, the amount of the biocide combinations of the present invention to control the growth of microorganisms is from 100 ppm to 10,000 ppm active ingredient. Preferably, the active ingredients of the composition are present in an amount of at least 300 ppm, preferably at least 500 ppm, preferably at least 600 ppm, preferably at least 700 ppm. Preferably, the active ingredients of the composition are present in an amount of no more than 8,000 ppm, preferably no more than 6,000 ppm, preferably no more than 5,000 ppm, preferably no more than 4,000 ppm, preferably no more than 3,000 ppm, preferably no more than 2500 ppm, preferably no more than 2,000 ppm, preferably no more than 1,800 ppm, preferably no more than 1,600 ppm. Concentrations mentioned above are in a liquid composition containing the biocide combinations; biocide levels in the dry film coating will be higher.

The present invention also encompasses a method for preventing microbial growth in building materials, especially in dry film coatings, by incorporating any of the claimed biocide combinations into the materials.

EXAMPLES

Sample preparation: A single or blend of biocides was post added into white acrylic latex paint free of biocides to give a maximum total active ingredient/s concentration tested. This paint was then diluted with a biocide free acrylic latex paint to give targeted concentrations for the testing. Depending on the type of biocide blends tested, the total biocides concentrations varies from 200 to 5000 ppm. After biocides addition or dilution, each sample was hand mixed for at least a minute until uniformity is achieved. Each of the paint samples as well as a control sample (containing no biocide) were used to prepare films on black plastic-vinyl chloride/acetate copolymer panels (LENETA, Mahwah, N.J.) using a 3 mil (0.0762 mm) bird bar applicator. The panels were thoroughly dried for at least 2 days avoiding direct exposure to sunlight. Square discs (0.5 inch; 1.27 $cm^2$) were cut out from each panel and were used as the substrate for fungal and algal efficacy tests. This sample size allowed for an agar border when the sample disc was placed into the well of the test plate. Each sample was tested in duplicate Test conditions: The appropriate media (BOLD'S 3N for Chlorophytes, BG-11 for Cyanobacteria, and PDA for fungi) were used to support microbial growth. The test plates were maintained at room temp (25° C.-26° C.), in a cycled light-dark environment, for four weeks for algae. Plates for fungal challenge tests were maintained at 30 C for four weeks. At the end of the incubation period the samples were scored for percent area covered by visible microbial growth.

Algal Inoculum

| Organisms | abbreviation | ATCC | Type | Medium for testing |
|---|---|---|---|---|
| Gloeocapsa sp. | Gs | ATCC 29159 | Unicellular, Colonial Cyanobacteria | BG-11 |
| Oscillatoria sp. | Os | ATCC 29135 | Filamentous Cyanobacteria | BG-11 |
| Nostoc commune | Nc | CCAP 1453/29 | Unicellular, Cenobial Chlorophyte | Bold |
| Trentepohlia aurea + Trentepohlia odorata | Ta + To | UTEX LB 429 + CCAP 483/4 | Filamentous Chlorophyte | Bold |
| Chlorella sp. UTEX + Chlorella kessleri | Cs + Ck | ATCC 30582 + ATCC 11468 | Unicellular Chlorophyte | Bold |
| Calothrix parientina | Cp | UTEX LB 1952 | Filamentous Cyanobacteria | Bold |

Fungal Inoculum

| Organisms | abbreviation | ATCC # | Medium for Growth and Testing |
|---|---|---|---|
| Aspergillus niger | An | 9642 | PDA |
| Penicillium funiculosum | Pf | 11797 | PDA |
| Cladosporium herbarum | Ch | 11281 | PDA |
| Aureobasidium pullulans | Ap | 9348 | PDA |
| Trichoderma viride | Tv | 32630 | PDA |
| Alternaria alternata | Aa | 20084 | PDA |

Algal Efficacy Testing—Modified ASTM 5589

ASTM 5589 is a standard accelerated test method for determining resistance of various coatings (including paints) to algal defacement. To accommodate for high-throughput screening, this method was scaled down from petri plates to 6-well plates. A single coupon was placed with a pair of sterile forceps at the center of the agar plug (on top) with the painted surface facing upwards. Algal inoculums were prepared by mixing equal concentrations ($1 \times 10^6$ cfu/ml) and equal volumes (depending on number of samples to be inoculated) of like growing organisms.

In Flumetsulam+various IT synergy study, three pool of mixed algae were prepared as the test inoculum, *Gloeocapsa* sp. and *Oscillatoria* sp. a mix of cyanobacteria grown on BG-11 media; *Chlorella* sp., *Chlorella kessleri*, and *Nostoc commune* are unicellular chlorphytes that were mixed and grown on Bold media; *Trentepohlia aurea, Tretepohlia odorata*, and *Calotrix parientina* are filamentous algae that were mixed and grown on Bold media.

In Diclosulam+various IT synergy study, only two pools of mixed algae were prepared; *Gloeocapsa* sp. and *Oscillatoria* sp. grown on BG-11 media and *Chlorella* sp., *Chlorella kessleri, Nostoc commune, Trentepohlia aurea, Tretepohlia odorata*, and *Calotrix parientina* grown on Bold media Each well that contains a tested coupon was inoculated with 400 µl of organism mixture ($1 \times 10^6$ cfu/ml) making sure that the whole surface (paint film as well as the agar surrounding it) was evenly covered. The plates were incubated at room temp (25° C.-26° C.) with cyclic exposure to light (OTT-Lite model # OTL4012P, 40 Watt, 26KLumen) and dark phases, for a period of four weeks. The total area covered was evaluated at the end of each week according to percent area covered in 5% increments.

Fungal Efficacy Testing—Modified ASTM 5590

ASTM 5590 is a standard accelerated test method for determining resistance of various coatings (including paints) to fungal defacement. To accommodate for high-throughput screening, this method was scaled down from petri plates to 6-well plates. To set up the test, an agar plug was placed at the bottom of each well of the sterile 6-well plate. A single coupon was placed with a pair of sterile forceps at the center of the agar plug (on top) with the painted surface facing upwards. Fungal inoculums were prepared by mixing equal concentrations ($1 \times 10^6$ cfu/ml) and equal volumes (depending on number of samples to be tested) of like growing organisms. For Flumetsulam+various IT synergy study, three pools of mixed fungi were prepared as the test inoculum. *Cladosporium herbarum* was mixed with *Aureobasidium pullulans*; *Aspergillus niger* was mixed with *Penicillium funiculosum* and *Alternaria alternata* was mixed with *Trichoderma viride*. For Diclosulam+various IT synergy study, all above fungi were mixed as a single pool. Each well was inoculated with 400 µl of organism mixture ($1 \times 10^6$ cfu/ml) making sure that the whole surface (paint film as well as the agar surrounding it) was evenly covered. The plates were incubated at 30° C. in presence of moisture, for a period of four weeks. The total percent area covered was evaluated and recorded at the end of each week after the $2^{nd}$ week and recorded in increments of 5%.

Synergy Index calculation

Synergy Index (SI)

The SI is calculated based on F.C.Kull et. Al. method (Applied Microbiology, Vol. 9 (1961). In this study, SI was calculated based on the following formula with the minimum inhibitory concentration chosen based on the percent inhibitory exhibited by the individual biocide against each microorganisms tested.

$$SI = Qa/QA + Qb/QB$$

Qa=the concentration of Biocide A in the blend
QA=The concentration of Biocide A as the only biocide
Qb=The concentration of Biocide B in the blend
QB=The concentration of Biocide B as the only biocide
SI value of <1 in the formula indicates a synergism of the blended biocides exists.

Note: If any of the active with maximum concentration tested did not exhibit some inhibition, this maximum concentration is used to calculate the estimated SI and a sign of less than (<) is included to take into account that higher concentration of the active is needed to achieve the targeted inhibition NE=no end point at the concentration tested that will meet the percent inhibition criteria set in each SI calculation Flumetsulam: DIMTS Synergy Study Synergy Study of Diclosulam and DIMTS

| Ratios | Aa + Tv + An + Pf + Ap + Ch | Cp + To + Ta + Cs + Ck + Nc | Gs + Os |
|---|---|---|---|
| 1Diclosulam:1 DIMTS | | | |
| Total conc, ppm | 3000 | 3000 | 1490 |
| % inhibition | 0 | 60 | 90 |
| SI | <1 | 5.8 | 1.2 |
| 1Dicolosulam:2 DIMTS | | | |
| Total conc, ppm | 3000 | 3000 | 750 |
| % inhibition | 0 | 50 | 85 |
| SI | <1 | 5.4 | 0.5 |
| 1Diclosulam:4 DIMTS | | | |
| Total conc, ppm | 3125 | 3125 | 1563 |
| % inhibition | 0 | 70 | 90 |
| SI | <1.1 | 5.4 | 0.9 |

| | AaTv | AnPf | ApCh | Cp + To + Ta | Cs + Ck + Nc | Gs + Os |
|---|---|---|---|---|---|---|
| 1Flumet:1 DIMTS | | | | | | |
| Total conc, ppm | 750 | 750 | 750 | 3000 | 1500 | 750 |
| % inhibition | 80 | 90 | 95 | 70 | 100 | 85 |
| SI | 0.26 | 0.7 | 0.7 | 1.6 | <0.81 | 0.7 |
| 1Flumet:3 DIMTS | | | | | | |
| Total conc, ppm | 750 | 750 | 750 | 2250 | 750 | 750 |
| % inhibition | 80.0 | 80 | 95 | 95 | 100 | 90 |
| SI | 0.28 | 1.0 | 1.0 | 1.5 | <0.50 | 1.0 |
| 1Flumet:5 DIMTS | | | | | | |
| Total conc, ppm | 750 | 750 | 750 | 1500 | 750 | 1500 |
| % inhibition | 75 | 100 | 95 | 95 | 97.5 | 85 |
| SI | 0.29 | 1.0 | 1.0 | 1.1 | <0.54 | 2.1 |
| 1Flumet:10DIMTS | | | | | | |
| Total conc, ppm | 751 | 751 | 751 | 3000 | 1500 | 751 |
| % inhibition | 90 | 100 | 95 | 95 | 100 | 95 |
| SI | 0.29 | 1.1 | 1.1 | 2.3 | <1.1 | 1.1 |
| 6Flumet:1 DIMTS | | | | | | |
| Total conc, ppm | 725 | 725 | 725 | 1400 | 725 | 725 |
| % inhibition | 75 | 90 | 92.5 | 95 | 90 | 87.4 |
| SI | 0.21 | 0.3 | 0.3 | 0.5 | <0.26 | 0.4 |
| 4Flumet:1 DIMTS | | | | | | |
| Total conc, ppm | 812.5 | 812.5 | 812.5 | 812.5 | 1625 | 812.5 |
| % inhibition | 75 | 95 | 95 | 95 | 100 | 90 |
| SI | 0.25 | 0.5 | 0.5 | 0.3 | <0.63 | 0.5 |
| 2Flumet:1 DIMTS | | | | | | |
| Total conc, ppm | 1500 | 750 | 750 | 1500 | 750 | 1500 |
| % inhibition | 80 | 80 | 90 | 95 | 100 | 80 |
| SI | 0.49 | 0.5 | 0.5 | 0.7 | <0.34 | 1.2 |
| Flumetsulam | | | | | | |
| Total conc, ppm | 3500 | 3500 | 3500 | 3500 | 3500 | 2625 |
| % inhibition | 70 | 40 | 70 | 95 | 0 | 80 |
| DIMTS | | | | | | |
| Total conc, ppm | 2500 | 625 | 625 | 1250 | 1250 | 625 |
| % inhibition | 70 | 100 | 100 | 100 | 100 | 85 |

| Ratios | Aa + Tv + An + Pf + Ap + Ch | Cp + To + Ta + Cs + Ck + Nc | Gs + Os |
|---|---|---|---|
| 1Diclosulam:6 DIMTS | | | |
| Total conc, ppm | 2800 | 2800 | 1400 |
| % inhibition | 0 | 60 | 85 |
| SI | <1 | 4.7 | 0.7 |
| 1Diclosulam:10 DIMTS | | | |
| Total conc, ppm | 2750 | 2750 | 687.5 |
| % inhibition | 0 | 80 | 85 |
| SI | <1 | 4.5 | 0.3 |
| 5Diclosulam:1 DIMTS | | | |
| Total conc, ppm | 3000 | 3000 | 750 |
| % inhibition | 0 | 75 | 85 |
| SI | <0.9 | 6.5 | 0.8 |
| 3Diclosulam:1 DIMTS | | | |
| Total conc, ppm | 3000 | 3000 | 750 |
| % inhibition | 0 | 75 | 85 |
| SI | <0.9 | 6.3 | 0.7 |
| 10Diclosulam:1 DIMTS | | | |
| Total conc, ppm | 3000 | 3000 | 3000 |
| % inhibition | 0 | 80 | 85 |
| SI | <0.9 | 6.6 | 0.8 |
| Diclosulam | | | |
| Total conc, ppm | 3500 | 437.5 | 875 |
| % inhibition | 0 | 100 | 85 |
| DIMTS | | | |
| Total conc, ppm | 2500 | 625 | 2500 |
| % inhibition | 0 | 100 | 85 |

The invention claimed is:

1. A synergistic antimicrobial composition comprising: (a) flumetsulam or diclosulam; and (b) diiodomethyl-p-tolylsulfone; wherein a weight ratio of flumetsulam to diiodomethyl-p-tolylsulfone is from 8:1 to 1:15 and a weight ratio of diclosulam to diiodomethyl-p-tolylsulfone is from 12:1 to 2:1 or 1:1.5 to 1:15.

2. The composition of claim 1 comprising flumetsulam and diiodomethyl-p-tolylsulfone; wherein the weight ratio of flumetsulam to diiodomethyl-p-tolylsulfone is from 6:1 to 1:10.

3. The composition of claim 1 comprising diclosulam and diiodomethyl-p-tolylsulfone; wherein the weight ratio of diclosulam to diiodomethyl-p-tolylsulfone is from 10:1 to 3:1 or 1:2 to 1:10.

4. The composition of claim 1 which is a building material.

5. The composition of claim 4 in which the building material is a paint, coating, polymer, plastic, synthetic or natural rubber, paper product, fiberglass sheet, insulation, exterior insulating finishing system, roofing or flooring felt, building plaster, wood product or wood-plastic composite.

* * * * *